United States Patent [19]

O'Lenick, Jr. et al.

[11] Patent Number: 5,091,493

[45] Date of Patent: Feb. 25, 1992

[54] SILICONE PHOSPHOBETAINES

[75] Inventors: Anthony J. O'Lenick, Jr., Lilburn; Jeff K. Parkinson, Lawrenceville, both of Ga.

[73] Assignee: Siltech Inc., Norcross, Ga.

[21] Appl. No.: 733,695

[22] Filed: Jul. 22, 1991

Related U.S. Application Data

[63] Continuation-in-part of Ser. No. 546,358, Jun. 27, 1990.

[51] Int. Cl.$^5$ ............................................. C08G 77/22
[52] U.S. Cl. ........................................ 528/30; 528/33; 525/474; 556/450
[58] Field of Search .................... 528/33, 30; 525/474; 556/450

[56] References Cited

FOREIGN PATENT DOCUMENTS 0292760 11/1988 European Pat. Off. .

Primary Examiner—Melvyn I. Marquis

[57] ABSTRACT

The present invention relates to a series of novel silicone phosphobetaines which are high foaming low irritation surface active agents that are substantive to fiber and hair. The compounds, because they contain a pendant ionizable phosphate group and a quatarnary amine compound are amphoterics that is they contain both a positive and negative charge in the same molecule. Since the compounds of the present invention are high molecular weight silicone polymers, they have a high degree of oxidative stability, even at elevated temperatures. In addition, these compounds are non volatile and nonirritating. These combination of properties makes these polymers ideally suited for use in personal care applications.

17 Claims, No Drawings

SILICONE PHOSPHOBETAINES

RELATED APPLICATIONS

This application is a continuation in part of copending application Ser. No. 07/546,358 filed 06/27/1990.

BACKGROUND OF THE INVENTION

(1) Field of Invention

The present invention relates to a series of novel silicone phosphobetaines which are high foaming low irritation surface active agents that are substantive to fiber and hair. The compounds, because they contain a pendant ionizable phosphate group and a quatarnary amine compound are amphoterics that is they contain both a positive and negative charge in the same molecule. Since the compounds of the present invention are high molecular weight silicone polymers, they have a high degree of oxidative stability, even at elevated temperatures and are nonirritating to skin and eyes. In addition, these compounds are non volatile and exhibit a inverse cloud point. These combination of properties makes these polymers ideally suited for use in personal care applications.

The compounds of the present invention are based upon raw materials which are prepared by the phosphation of a pendant hydroxyl group which is present on a silicone polymer. The phosphated silicone polymers are subject of a copending application upon which this is a continuation in part.

The technology used to produce the phosphobetaines of the present invention is very flexible and allows us to prepare performance tailored molecules for specific applications.

(2) Description of the Arts and Practices

Silicone oils (dimethylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not ionically bonded the effect is very transient. The product is removed with one washing.

Fatty Phosphobetaines have been known since 1974. There are several patents which have issued on this topic.

U.S. Pat. No. 3,856,893 and 3,928,509 both issued to Diery disclose the basic technology used to make phosphobetaines.

Later, amido and imidazoline based phosphobetaines were patented in U.S. Pat. No. 4,209,449 issued in 1980 to Mayhew and O'Lenick. This patent teaches that phosphate quats can be prepared by the reaction of a phosphate salt, three equivalents of epichlorohydrin and in a subsequent step, three equivalents of a tertiary amine.

U.S. Pat. No. 4,215,064 issued in 1980 to Lindemann et al teaches the basic technology that is used for the preparation of amido and imidazoline based phosphobetaines. These compounds can be prepared by the reaction of a phosphate salt, one equivalent of epichlorohydrin and one equivalent of a tertiary amine.

U.S. Pat. No. 4,243,602 issued in 1981 to O'Lenick and Mayhew teaches the basic technology that is used for the preparation of phosphobetaines based upon phosphorous acid salts. These compounds can be prepared by the reaction of a phosphorous acid salt, one equivalent of epichlorohydrin and one equivalent of a tertiary amine.

U.S. Pat. No. 4,261,911 issued in 1981 to Lindemann et al teaches the utilization of phosphobetaines based upon phosphorous acid. These compounds are useful as surfactants.

U.S. Pat. No. 4,283,542 issued in 1981 to O'Lenick and Mayhew teaches the process technology used for the preparation of phosphobetaines. These compounds can be prepared by the reaction of a phosphate salt, one equivalent of epichlorohydrin and one equivalent of a tertiary amine.

U.S. Pat. No. 4,336,386 issued in 1982 to O'Lenick and Mayhew teaches the technology for the preparation of imidazoline derived phosphobetaines based upon phosphorous acid salts. These compounds can be prepared by the reaction of a phosphorous acid salt, one equivalent of epichlorohydrin and one equivalent of an imidazoline.

U.S. Pat. No. 4,503,002 which is related to U.S. Pat. No. 4,209,449 issued in 1985 to Mayhew and O'Lenick teach that phosphate quats can be prepared by the reaction of a phosphate salt, three equivalents of epichlorohydrin and three equivalents of a tertiary amine.

Despite the fact that there was significant patenting of phosphobetaine compounds based upon phosphoric acid salts, phosphorous acids salts, tertiary amines and imidazolines, the technology needed to place a silicone moiety into the molecule and make the compounds of the present invention was not available until the it was discovered that silicone phosphates could be prepared and that they represent starting materials for the preparation of silicone phosphobetaines. Silicone phosphates are the basic raw material used for the preparation of silicone based phosphobetaines. The current application is a continuation in part of the copending patent application which discloses how to make the silicone phosphates. It was also not until the compounds of the present invention that the concept and technology needed to incorporate silicone into the phosphobetaine was created. The beneficial effects of lowering irritation, providing increased substantivity to both hair and skin and antistatic properties were never anticipated by the references.

THE INVENTION

(1) Object of the Invention

It is the object of the present invention to provide a series of novel silicone phosphobetaines which are high foaming, low irritation to eyes and skin, have an inverse cloud point and are substantive to the surface of a fibers.

Still another object of the present invention is to provide a series of silicone phosphobetaines which have differing solubilities in water and organic solvents. This is achieved by selection of the phosphated silicone polymer used as a raw material and the amine chosen for preparation of the phosphobetaine.

Application of the compounds of the invention can be from solvent, aqueous dispersion or solution, or applied neat in these processes.

The phosphated silicone polymers, suitable as raw materials, in a preferred embodiment, contain varying amounts of ethylene oxide, propylene oxide or butylene oxide or mixtures thereof. The presence of the oxide in the phosphated silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to skin, hair and fiber.

In another preferred embodiment a is an integer from 10 to 100; b is an integer from 10 to 100; and c is an integer from 5 to 20.

In still another preferred embodiment x, y and z are independently integers ranging from 1 to 10.

2) Summary of the Invention

The present invention relates to a series of novel silicone phosphobetaines. These compounds have one or more pendant phosphate functional group connected via a hydroxypropyl group to a amine group. The amine group typically will be quaternized nitrogen. Hence the products are amphoterics having both an anionic and cationic group present on the same pendant group. The silicone polymer by virtue of this unique pendent group is highly foaming, non irritating to eyes and skin and deposits on fiber surfaces and form effective surface modifying finishes. The compounds of the present invention are therefore very well suited to applications in the personal care market.

The compounds of this invention having a pendant amphoteric group is represented by the following formula;

$$(R-O)-\overset{O}{\underset{(O-CH_2-CH(OH)CH_2-R^3\,Cl^\ominus)_e}{\overset{\|}{P}}}-(O^\ominus M^\oplus)_f$$

wherein
R is $-(CH_2CH_2O)_z-(CH_2CH(CH_3)O)_y-(CH_2CH_2O)_x-(CH_2)_3$

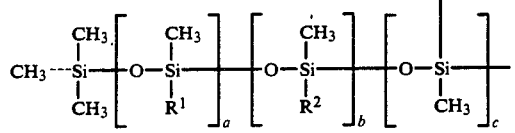

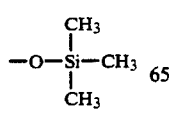

a is an integer from 0 to 200;

b is an integer from 0 to 200;
c is an integer from 1 to 200;
$R^1$ is selected from $-(CH_2)_nCH_3$ and phenyl;
n is an integer from 0 to 10;
$R^2$ is $-(CH_2)_3-(OCH_2CH_2)_x-(OCH_2CH(CH_3))_y-(OCH_2CH_2)_z-OH$;
x, y and z are integers and are independently selected from 0 to 20;
e is an integer ranging from 1 to 2;
f is 0 or 1 with the proviso that e+f=2;
M is selected from H, Na, K, Li or NH4;
$R^3$ is selected from

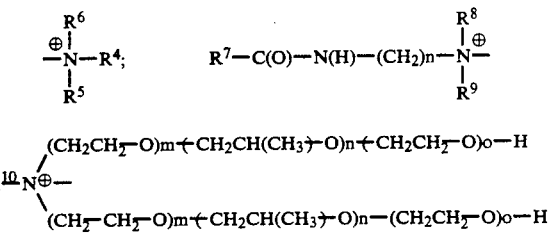

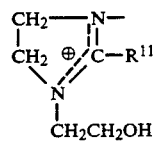

and

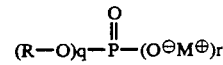

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are independently selected from lower alkyl having from one to 20 carbon atoms;
$R^{10}$ is alkyl having from 1 to 20 carbon atoms;
$R^{11}$ is alkyl having from 1 to 20 carbon atoms;
m, n, and o are independently integers each ranging from 0 to 20.

The reaction sequence needed to produce the compounds of the present invention starts with a silicone phosphate of the following structure;

$$(R-O)_q-\overset{O}{\overset{\|}{P}}-(O^\ominus M^\oplus)_r$$

wherein
R is $-(CH_2CH_2O)_z-(CH_2CH(CH_3)O)_y-(CH_2CH_2O)_x-(CH_2)_3$

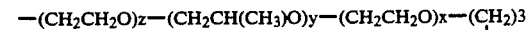

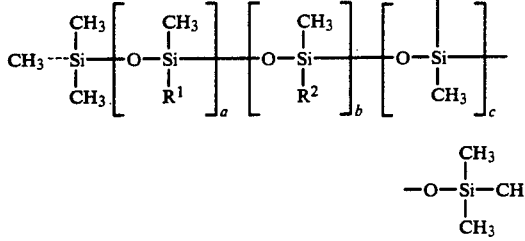

a is an integer from 0 to 200;
b is an integer from 0 to 200;
c is an integer from 1 to 200;

$R^1$ is selected from $-(CH_2)_nCH_3$ and phenyl;

n is an integer from 0 to 10;

$R^2$ is $-(CH_2)_3-(OCH_2CH_2)x-(OCH_2CH(CH_3))y-(OCH_2CH_2)z-OH$;

x, y and z are integers and are independently selected from 0 to 20;

q and r range from 1 to 2 with the proviso that q+r=3;

M is selected from H, Na, K, Li or $NH_4$.

These materials are items of commerce available from Siltech Inc. Norcross, Ga.

The reactive intermediates are prepared by the reaction of one or two mole equivalents of epichlorohydrin with an equivalent of silicone phosphate ester. The mono adduct is made by reacting one equivalent each of epicholorhydrin and one equivalent of silicone phosphate. The diadduct is made by reacting two equivalents of epicholorhydrin and one equivalent of silicone phosphate.

Mono Adduct

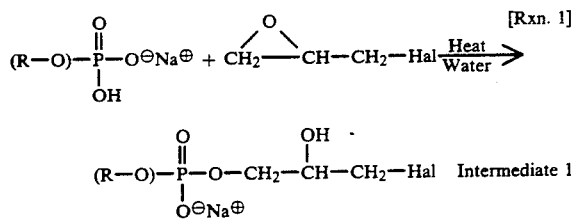

[Rxn. 1]

Hal is halogen.

Diadduct

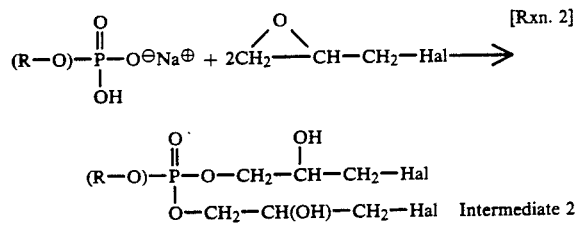

[Rxn. 2]

Hal is halogen.

PREFERRED EMBODIMENT

In one embodiment the tertiary amine is an tri alkyl amine conforming to the following structure;

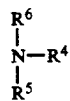

$R^4$ is alkyl having from 1 to 20 carbon atoms;
$R^5$ is alkyl having from 1 to 20 carbon atoms.
$R^6$ is alkyl having from 1 to 20 carbon atoms.

In a preferred embodiment the tertiary amine reacted with the silicone hydroxypropyl intermediate is an N alkyl amido, N diakyl amine.

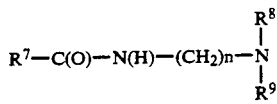

$R^7$ is alkyl having from 1 to 20 carbon atoms;

$R^8$ and $R^9$ are independently selected from lower alkyl having from one to three carbon atoms.

In an another preferred embodiment the tertiary amine reacted with the silicone hydroxypropyl intermediate is an imidazoline.

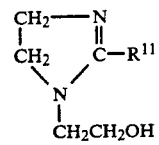

$R^{11}$ is alkyl having from 6 to 20 carbon atoms.

In still another preferred embodiment the tertiary amine reacted with the silicone hydroxypropyl intermediate is an bis alkoxyethyl amine conforming to the following structure;

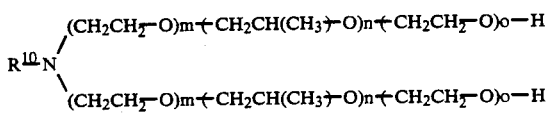

$R^{10}$ is alkyl having from 6 to 20 carbon atoms;

m, n, and o are independently integers each ranging from 0 to 20.

EXAMPLES

DIMETHICONE COPOLYOLS

The phosphate esters used as raw materials for the preparation of the compounds of the present invention are prepared by reaction of a hydroxyl containing silicone polymer with a suitable phosphating reagent.

One method of placing preparing the reactive hydroxyl containing silicone polymer is to react silanic hydrogen containing polymer with allyl alcohol or allyl alcohol alkoxylate monomer. Procedures this reaction are well known to those skilled in the art. U.S. Pat. No. 4,083,856 describe suitable processes.

EXAMPLES

Vinyl Intermediate Compounds

Compounds of this class are prepared by alkoxylation of allyl alcohol using methods well known to those skilled in the art. The following are some of the many compounds which can be used to make the products of this invention.

| $CH_2=CH-CH_2-O-(CH_2-CH_2-O)x-(CH_2-CH(CH_3)-O)y-(CH_2-CH_2-O)z-H$ | | | | |
|---|---|---|---|---|
| Designation | x | y | z | Molecular Weight |
| A | 3 | 0 | 0 | 189 |
| B | 9 | 27 | 3 | 2,178 |
| C | 11 | 3 | 0 | 718 |
| D | 0 | 0 | 0 | 57 |
| E | 20 | 20 | 20 | 2,940 |
| F | 20 | 0 | 0 | 880 |
| G | 10 | 10 | 10 | 1,470 |

Preparation of Intermediates

Silicone intermediates of the type used to make the compounds of this invention are well known to those skilled in the art. International Publication (*Silicone Alkylene Oxide Copolymers As Foam Contol Agents*) WO 86/0541 by Paul Austin (Sept. 25, 1986) p.16 (examples 1 to 6) teaches how to make the following intermediates, and is incorporated herein by reference.

Hydrosilation of Intermediates

Silanic Hydrogen Containing Compounds $$CH_3-\underset{\underset{M}{CH_3}}{\overset{CH_3}{Si}}-O-\underset{\underset{D}{CH_3}}{\overset{CH_3}{Si}}-O-\underset{\underset{D'}{H}}{\overset{CH_3}{Si}}-O-\underset{\underset{M}{CH_3}}{\overset{CH_3}{Si}}-CH_3$$

Group Designations

| Example | Austin Example | Group Designation | Average Molecular Weight | Equivalent Molecular Weight |
|---|---|---|---|---|
| 1 | 1 | $MD_{20} D'_{3.2} M$ | 1,850 | 551 |
| 2 | 4 | $MD_{160} D'_5 M$ | 24,158 | 4,831 |
| 3 | 6 | $MD_{20} D'_{10} M$ | 2,258 | 225 |

Hydrosilation Compounds

The hydrosilation reaction used to make the compounds of this invention are well known to those skilled in the art. Reference; International Publication (*Silicone Alkylene Oxide Copolymers As Foam Control Agents*) WO 86/0541 by Paul Austin (Sept. 25, 1986) p.19.

EXAMPLE 4

To a 22 liter three round bottom flask fitted with a mechanical agitator, thermometer with a Therm-o-watch temperature regulator, nitrogen sparge tube vented reflux condenser and heating mantle is added 189.0 grams of Vinyl Intermediate Example #A. Next add 225 grams of Silanic Hydrogen Containing Compound Example #3 and 3,000 grams of toluene. Heat to 115° C. to remove azeotropically remove any water and 200 ml of toluene. The temperature is reduced to 85° C. and 3.5 ml of 3% $H_2PtCl_6$ in ethanol is added. Light to then excluded from the flask by covering it with a black cloth. An exotherm is noted to about 95° C., while the contents are stirred for about 2 hours. During this time silianic hydrogen concentration drops to nil. Cool to 65° C. and slowly add 60 g of sodium bicarbonate, allow to mix overnight and filter through a 4 micron pad. Distill off any toluene at 100° C. and 1 torr.

EXAMPLE 5-10

The above procedure is repeated, only this time replacing both the silanic hydrogen compound #3 with the specified number of grams of the specified silanic hydrogen compound and the vinyl intermediate example A with the specified number of grams of the specified vinyl intermediate.

| | Vinyl Intermediate | | Silanic Hydrogen Compound | |
|---|---|---|---|---|
| Example | Example | Grams | Example | Grams |
| 4 | A | 189.0 | 1 | 551.0 |
| 5 | B | 2,178.0 | 2 | 4,831.0 |
| 6 | C | 718.0 | 3 | 225.0 |
| 7 | D | 57.0 | 1 | 551.0 |
| 8 | E | 2,940.0 | 2 | 4,831.0 |
| 9 | F | 880.0 | 3 | 225.0 |
| 10 | G | 1,470.0 | 1 | 551.0 |

PHOSPHATION

Phosphating Agents

Polyphosphoric Acid (PPA) is 115% phosphoric acid. When used as a phosphating agent is gives more mono ester than the phosphorus pentoxide.

Phosphorus pentoxide is $P_2O_5$. It is more aggressive in phosphation and results in more diester.

The silicone phosphates of this invention can be prepared by reacting the hydroxyl containing silicone polymer with a suitable phosphating agent. Preferred phosphating reagents are polyphosphoric acid and phosphorus pentoxide.

The preparation of the novel silicone phosphates of this invention from the hydroxy silicone compounds can be illustrated by the following reaction in which R is the hydroxy silicone compound.

Phosphation Reaction Sequence $R-OH + P_2O_5 \longrightarrow$ $(R-O)-P(O)-(OH)_2$ and $(R-O-)_2P(O)-(OH)$ ↓ Neutralization KOH/Water $(R-O)-P(O)-(OK)_2$ and $(R-O-)_2P(O)-(OK)$ It will be understood by the above reaction that the product of phosphation, weather using polyphosphoric acid or phosphorus pentoxide give a mixture of mono and di ester.

The following examples further illustrate the objects and advantages of this invention, though it should be understood that the various reactants and amounts thereof, reaction conditions, and other details are merely illustrative and should not be construed to unduly limit this invnetion.

GENERAL PROCEDURE

The preparation of the phosphobetaine of the current invention requires several steps. These steps in order are (a) phosphation, (b) dilution in water and neutralization with base, (c) the reaction with epichlorohydrin with the aqueous, silicone phosphate salt, (d) and the reaction with the amine with the halo-hydroxypropyl silicone. It is advantageous to run these reactions in the same reaction vessel, one process right after the other. This "tandem type reaction" sequence is preferred, but not required. Examples given here employ the tandem reaction technique.

(a) Phosphation

The specified amount of hydroxy silicone compound (Examples 4-10) is added to a suitable reaction vessel. The specified amount of either polyphosphoric acid or phosphorus pentoxide is charged to under good agitation over a 2 hr. period. The exothermic reaction raises the temperature of the mixture to about 70° C. After 1 hour slowly raise the temperature to 100° C. and hold 2-4 hours.

| | Hydroxy Silicone | | Polyphosphoric Acid |
|---|---|---|---|
| Example | Example | Grams | Grams |
| 11 | 4 | 740.0 | 56.5 |
| 12 | 5 | 7009.0 | 56.5 |

-continued

| | | | |
|---|---|---|---|
| 13 | 6 | 943.0 | 56.5 |
| 14 | 7 | 608.0 | 56.5 |
| 15 | 8 | 7771.0 | 56.5 |
| 16 | 9 | 1105.0 | 56.5 |
| 17 | 10 | 2021.0 | 56.5 |

| | Phosphorus Pentoxide | | |
|---|---|---|---|
| | Hydroxy Silicone | | Phosphorus Pentoxide |
| Example | Example | Grams | Grams |
| 18 | 11 | 798.0 | 36.0 |
| 19 | 12 | 7067.0 | 36.0 |
| 20 | 13 | 1001.0 | 36.0 |
| 21 | 14 | 666.0 | 36.0 |
| 22 | 15 | 7829.0 | 36.0 |
| 23 | 16 | 1163.0 | 36.0 |
| 24 | 17 | 2079.0 | 36.0 |

(b) dilution in water and neutralization with base

The compounds of examples 11-24 are neutralized to pH 10.4 with 20% aqueous base. The following bases are used; NaOH, KOH, LiOH, NH4OH. The solids are then adjusted to 50% with water.

| Example | Phosphated Silicone Example | Base Type |
|---|---|---|
| 25 | 11 | KOH |
| 26 | 12 | NaOH |
| 27 | 13 | LiOH |
| 28 | 14 | NH4OH |
| 29 | 15 | KOH |
| 30 | 16 | NaOH |
| 31 | 17 | KOH |
| 32 | 19 | NaOH |
| 33 | 19 | KOH |
| 34 | 20 | NaOH |
| 35 | 21 | KOH |
| 36 | 22 | NaOH |
| 37 | 23 | KOH |
| 38 | 24 | NaOH |

INTERMEDIATE PREPARATION
(Epichlorohydrin Reaction)

(c) the reaction with epichlorohydrin with the aqueous, silicone phosphate salt

As will be understood by the reaction sequences above there are two distinct reaction possibilities, namely the mono adduct and the diadduct. (Intermediate 1 and 2 respectively).

Mono Adducts Reactions: EXAMPLES 39-52

| Example | Phosphate Salt Example Number | Epichlorohydrin |
|---|---|---|
| 39 | 25 | 46.0 Grams |
| 40 | 26 | 46.0 Grams |
| 41 | 27 | 46.0 Grams |
| 42 | 28 | 46.0 Grams |
| 43 | 29 | 46.0 Grams |
| 44 | 30 | 46.0 Grams |
| 45 | 31 | 46.0 Grams |
| 46 | 32 | 46.0 Grams |
| 47 | 33 | 46.0 Grams |
| 48 | 34 | 46.0 Grams |
| 49 | 35 | 46.0 Grams |
| 50 | 36 | 46.0 Grams |
| 51 | 37 | 46.0 Grams |
| 52 | 38 | 46.0 Grams |

EXAMPLES 53-66 (Di Adduct Reactions)

| Example | Phosphate Salt Example Number | Epichlorohydrin |
|---|---|---|
| 53 | 25 | 92.5 Grams |
| 54 | 26 | 92.5 Grams |
| 55 | 27 | 92.5 Grams |
| 56 | 28 | 92.5 Grams |
| 57 | 29 | 92.5 Grams |
| 58 | 30 | 92.5 Grams |
| 59 | 31 | 92.5 Grams |
| 60 | 32 | 92.5 Grams |
| 61 | 33 | 92.5 Grams |
| 62 | 34 | 92.5 Grams |
| 63 | 35 | 92.5 Grams |
| 64 | 36 | 92.5 Grams |
| 65 | 37 | 92.5 Grams |
| 66 | 38 | 92.5 Grams |

Raw Material Amines

Class 1: Alkyl Tertiary amines

$R^4$ is alkyl having from 1 to 20 carbon atoms;
$R^5$ is alkyl having from 1 to 20 carbon atoms;
$R^6$ is alkyl having from 1 to 20 carbon atoms;

| Raw Material Example | $R^4$ | $R^5$ | $R^6$ | Molecular Weight |
|---|---|---|---|---|
| A | CH3 | C12H25 | CH3 | 213.0 |
| B | C2H5 | C6H13 | C2H5 | 143.0 |
| C | CH3 | C8H17 | CH3 | 143.0 |
| D | CH3 | C10H21 | CH3 | 171.0 |
| E | CH3 | C18H37 | CH3 | 283.0 |
| F | CH3 | C20H41 | CH3 | 311.0 |
| G | C6H13 | C6H13 | CH3 | 185.0 |
| H | CH3 | C10H21 | C10H21 | 297.0 |

Class 2: Alkyl amido Amines

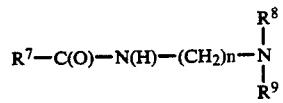

$R^7$ is alkyl having from 1 to 20 carbon atoms;
$R^8$ and $R^9$ are independently selected from lower alkyl having from one to three carbon atoms.

| Raw Material Example | $R^7$ | $R^8$ | $R^9$ | Molecular Weight |
|---|---|---|---|---|
| I | C7H15 | CH3 | CH3 | 129.0 |
| J | C11H23 | CH3 | CH3 | 185.0 |
| K | C13H27 | CH3 | CH3 | 213.0 |
| L | C17H35 | CH3 | CH3 | 269.0 |
| M | C19H39 | C2H5 | C2H5 | 325.0 |
| N | C6H13 | C2H5 | C2H5 | 143.0 |
| O | C20H21 | C2H5 | C2H5 | 319.0 |
| P | C11H23 | C2H5 | C2H5 | 213.0 |

Class 3: Alkyl alkoxy amines

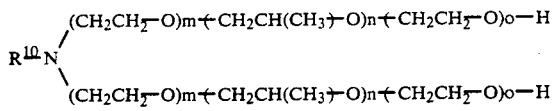

$R^{10}$ is alkyl having from 6 to 20 carbon atoms;
m, n, and o are independently integers each ranging from 0 to 20.

| Raw Material Example | $R^{10}$ | m | n | o | Molecular Weight |
|---|---|---|---|---|---|
| Q | C6H13 | 20 | 20 | 20 | 3,039.0 |
| R | C10H21 | 0 | 0 | 0 | 155.0 |
| S | C12H25 | 5 | 1 | 5 | 682.0 |
| T | C18H37 | 0 | 10 | 0 | 857.0 |
| U | C20H21 | 5 | 1 | 10 | 994.0 |

Class 4: Imidazoline Amines

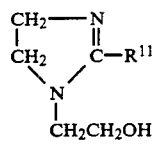

$R^{11}$ is alkyl having from 6 to 20 carbon atoms.

| Raw Material Example | $R^{11}$ | Molecular Weight |
|---|---|---|
| V | C7H15 | 186.0 |
| W | C11H23 | 242.0 |
| X | C17H35 | 326.0 |
| Y | C19H40 | 355.0 |
| Z | C6H13 | 172.0 |

PHOSPHOBETAINE PREPARATION

General Procedure

To the reaction product of epichlorohydrin with the aqueous, silicone phosphate salt prepared above in the specified example (examples 39–66) is added the specified number of grams of the specified amine reactant (Examples A-Z). Water is then added to make the solids 40%.

The resulting reaction mass is heated to 85°–90° C. and held for 4–6 hours. The pH is kept at or slightly above 7 by additions of small amounts of aqueous base, if needed. The batch clears and the desired phosphobetaine is obtained and used without purification. The reaction progress if followed by the percentage of inorganic chloride ion present. The reaction is complete when 97% of theoretical inorganic chloride ion has been generated.

EXAMPLES 67–93

| Example Number | Phopshobetaine Intermediate Example | Amine Reactant Example | Grams |
|---|---|---|---|
| 67 | 39 | A | 106.5 |
| 68 | 40 | B | 71.5 |
| 69 | 41 | C | 71.5 |
| 70 | 42 | D | 85.5 |
| 71 | 43 | E | 141.5 |
| 72 | 44 | F | 155.5 |

-continued

| Example Number | Phopshobetaine Intermediate Example | Amine Reactant Example | Grams |
|---|---|---|---|
| 73 | 45 | G | 92.5 |
| 74 | 46 | H | 148.5 |
| 75 | 47 | I | 64.5 |
| 76 | 48 | J | 92.5 |
| 77 | 49 | K | 106.5 |
| 78 | 50 | L | 134.5 |
| 79 | 51 | M | 229.8 |
| 80 | 52 | N | 71.5 |
| 81 | 53 | O | 319.0 |
| 82 | 54 | P | 213.0 |
| 83 | 55 | Q | 3,039.0 |
| 84 | 56 | R | 155.0 |
| 85 | 57 | S | 682.0 |
| 86 | 58 | T | 857.0 |
| 87 | 59 | U | 994.0 |
| 88 | 60 | V | 186.0 |
| 89 | 61 | W | 242.0 |
| 90 | 62 | X | 326.0 |
| 91 | 63 | Y | 355.0 |
| 92 | 64 | Z | 172.0 |
| 93 | 65 | A | 213.0 |
| 94 | 66 | B | 143.0 |
| 95 | 53 | C | 143.0 |
| 96 | 54 | D | 171.0 |
| 97 | 55 | E | 283.0 |
| 98 | 56 | F | 311.0 |
| 99 | 57 | G | 185.0 |
| 100 | 58 | H | 297.0 |
| 101 | 59 | I | 129.0 |
| 102 | 60 | J | 185.0 |
| 103 | 61 | K | 213.0 |
| 104 | 61 | L | 269.0 |
| 105 | 63 | M | 325.0 |
| 106 | 64 | N | 143.0 |
| 107 | 39 | O | 159.5 |
| 108 | 40 | P | 106.5 |
| 109 | 41 | Q | 1,519.5 |
| 110 | 42 | R | 77.5 |
| 111 | 43 | S | 341.0 |
| 112 | 44 | T | 428.5 |
| 113 | 45 | U | 497.0 |
| 114 | 46 | V | 93.0 |
| 115 | 47 | W | 121.0 |
| 116 | 48 | X | 163.0 |
| 117 | 49 | Y | 177.5 |
| 118 | 50 | Z | 86.0 |

APPLICATIONS EXAMPLES

The compounds of the present invention produce a copious thick foam when diluted to 1% active in cylinder shake foam tests.

The compounds of the present invention are very mild to the skin, eyes and mucous membrane when applied at 10% active.

The compounds of the present invention are not toxic when tested in LD 50 tests.

All of these attributes make the compounds of the present invention candidates for use in personal care compositions.

What is claimed:

1. A silicone phosphobetaine which conforms to the following structure;

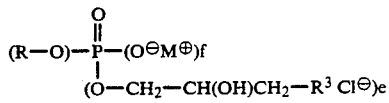

wherein
R is

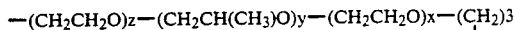

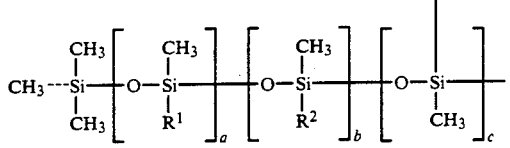

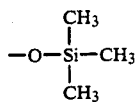

a is an integer from 0 to 200;
b is an integer from 0 to 200;
c is an integer from 1 to 200;
$R^1$ is selected from $-(CH_2)_nCH_3$ or phenyl;
n is an integer from 0 to 10;
$R^2$ is $-(CH_2)_3-(OCH_2CH_2)x-(OCH_2CH(CH_3))y-(OCH_2CH_2)z-OH$;
x, y and z are independently integers ranging from 0 to 20;
e is an integer ranging from 1 to 2;
f is 0 or 1 with the proviso that e+f=2;
M is selected from H, Na, K, Li or $NH_4$;
$R^3$ is selected from

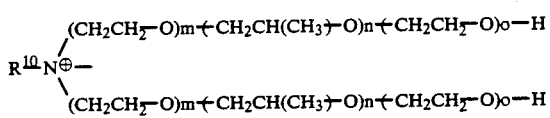

or

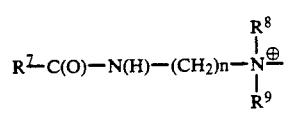

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ is alkyl having from 1 to 20 carbon atoms;
$R^9$ is alkyl having from 1 to 20 carbon atoms;
$R^{10}$ is alkyl having from 1 to 20 carbon atoms;
$R^{11}$ is alkyl having from 1 to 20 carbon atoms;
m, n, and o are independently integers each ranging from 0 to 20.

2. A compound of claim 1 wherein;
$R^3$ is

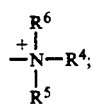

$R^4$ is alkyl having from 1 to 20 carbon atoms;
$R^5$ is alkyl having from 1 to 20 carbon atoms;

$R^6$ is alkyl having from 1 to 20 carbon atoms.

3. A compound of claim 1 wherein;
$R^3$ is $$R^7-C(O)-N(H)-(CH_2)n-\overset{\overset{R^8}{|}}{\underset{\underset{R^9}{|}}{N}}-$$

$R^7$ is alkyl having from 1 to 20 carbon atoms;
$R^8$ is alkyl having from 1 to 20 carbon atoms;
$R^9$ is alkyl having from 1 to 20 carbon atoms.

4. A compound of claim 1 wherein;
$R^3$ is

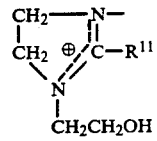

$R^{10}$ is alkyl having from 1 to 20 carbon atoms;
m, n, and o are independently integers each ranging from 0 to 20.

5. A compound of claim 1 wherein
$R^3$ is $R^{11}$ is alkyl having from 1 to 20 carbon atoms.

6. A compound of claim 2 wherein
a is an integer from 10 to 100;
b is an integer from 10 to 100;
c is an integer from 5 to 20.

7. A compound of claim 3 wherein
a is an integer from 10 to 100;
b is an integer from 10 to 100;
c is an integer from 5 to 20.

8. A compound of claim 4 wherein
a is an integer from 10 to 100;
b is an integer from 10 to 100;
c is an integer from 5 to 20.

9. A compound of claim 5 wherein
a is an integer from 10 to 100;
b is an integer from 10 to 100;
c is an integer from 5 to 20.

10. A compound of claim 2 wherein x, y and z are independently integers ranging from 1 to 10.

11. A compound of claim 3 wherein x, y and z are independently integers ranging from 1 to 10.

12. A compound of claim 4 wherein x, y, and z are independently integers ranging from 1 to 10.

13. A compound of claim 5 wherein x, y and z are independently integers ranging from 1 to 10.

14. A compound of claim 2 wherein $R^4$ and $R^5$ are each $CH_3$; $R^6$ is alkyl having between 12 and 18 carbon atoms.

15. A compound of claim 3 wherein $R^8$ and $R^9$ are each $CH_3$; $R^7$ is alkyl having between 12 and 18 carbon atoms.

16. A compound of claim 4 wherein m, n and o are independently integers from 0 to 5; $R^{10}$ is alkyl having between 12 and 18 carbon atoms.

17. A compound of claim 5 wherein $R^{11}$ is alkyl having between 12 and 18 carbon atoms.

* * * * *